US00PP24655P3

(12) United States Plant Patent
Coiner

(10) Patent No.: US PP24,655 P3
(45) Date of Patent: Jul. 22, 2014

(54) HYBRID TEA ROSE PLANT NAMED 'VELVET ORANGE'

(50) Latin Name: *Rosa hybrida*
Varietal Denomination: Velvet Orange

(76) Inventor: James W. Coiner, Covina, CA (US)

( * ) Notice: Subject to any disclaimer, the term of this patent is extended or adjusted under 35 U.S.C. 154(b) by 101 days.

(21) Appl. No.: 13/573,324

(22) Filed: Sep. 11, 2012

(65) Prior Publication Data

US 2014/0075613 P1 Mar. 13, 2014

(51) Int. Cl.
*A01H 5/00* (2006.01)

(52) U.S. Cl.
USPC ..... Plt./135; Plt./130

(58) Field of Classification Search
USPC ..... Plt./130, 135
See application file for complete search history.

*Primary Examiner* — Susan McCormick Ewoldt
(74) *Attorney, Agent, or Firm* — Christie, Parker & Hale, LLP

(57) ABSTRACT

A new variety of Hybrid Tea rose suitable for garden decoration, having flowers of orange blend coloration.

1 Drawing Sheet

Classification: The present invention relates to a new *Rosa hybrida* plant.

Variety denomination: The new plant has the varietal denomination 'VELVET ORANGE'.

BACKGROUND OF THE INVENTION

This invention relates to a new and distinct variety of Hybrid Tea Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor is the following combination of characteristics: The plant has a compact upright growing growth habit, suitable for outdoor garden decoration.

Asexual reproduction of the new variety by budding as performed in Kern County Calif., shows that the foregoing and other distinguishing characteristics come true to form and are established and transmitted through succeeding asexual propagations. 'Velvet Orange' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Bronze Sunset (U.S. Plant Pat. No. 16,329), by the following combination of characteristics: This rose has unique double blended coloring along with deep green hardy foliage.

BRIEF DESCRIPTION OF ILLUSTRATION

The accompanying photograph, FIG. 1, illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers singly, sometimes in clusters of two to three or more per stem. Flowers may be borne in irregular rounded clusters on strong medium to long stems (about 34 cm to about 40 cm). Outdoors, the plant blooms nearly continuously during the growing season. The flowers have a slight tea to fruity fragrance.

BUD

The peduncle is about 5 cm to about 7 cm in length, of average to heavy caliper and usually erect. It is moderately rough, with many stipitate glands, and many hairs and prickles. Peduncle color is near between 144b and 144c.

Before the calyx breaks, the bud is about 1 cm to about 2.3 cm in diameter at the widest point, about 1.1 cm to about 2.6 cm in length, and pointed to ovoid in shape with a conspicuous neck. The surface of the bud bears some foliaceous appendages, stipitate glands and glandular bloom, usually with slender bristle-like foliaceous parts extending beyond the tip of the bud about ¼ or more of its length. Bud color is near between 32a and 32b.

The sepals are about 2.6 cm to about 3.6 cm in length and about 1 cm to about 1.7 cm in width at the widest point. The outer surface color of the sepal is near between 144b and 144d sometimes often lightly suffused, especially on the side exposed to the sun, with near between 147b and 147c. The inner surface color of the sepal is near between 148c and 148d and covered with fine tomentum; sepal margins are lined with some stipitate glands and hairs.

The receptacle of the flower is of moderately short to medium length (about 5 cm to about 7.1 cm) and average in caliper. The receptacle is somewhat pointed to ovoid in form. Its surface is somewhat hairy and rough with somewhat thick dry walls. The receptacle color is near between 144b and 144d.

As the petals open (after the calyx breaks), the bud is about 2.1 cm to about 2.9 cm in diameter at the widest point, about 3.1 cm to about 4.3 cm in length, and very moderately pointed to ovoid in form. The color of the under and upper surfaces of the newly opened petals is near between 30a and 32a. At the point where the petal attaches, there is a moderately small zone of near between 29a and 30d. The color of the upper surfaces of the newly opened petals is near between 32b and 32d.

BLOOM

When fully open, the bloom ranges from about 8 cm to about 10 cm in diameter. Petalage is double with about 25 to 33 petals and about 3 to 4 petaloids irregularly arranged. When partially open, the bloom form is somewhat full to high centered, and the petals are somewhat tightly spiraled to undulated with petal edges very moderately rolled outward. When fully open, the bloom form is somewhat full to globular, and the petals are somewhat moderately tightly cupped to undulated with petal edges moderately rolled outward.

PETALS

The substance of the petals is somewhat crisp and of medium to thick in thickness, with upper surfaces moderately velvety and under surfaces velvety to matte. The petals are about 4.0 cm to about 5.8 cm in length and about 3.8 cm to about 5.6 cm in width at the widest point. Petal margins are somewhat moderately dentate to smooth.

The outer petals are nearly round in shape with apices rounded and sometimes slightly notched with one to two notches.

The inner petals are moderately round in shape with apices very rounded to flat sometimes slightly notched with one to two notches.

Petaloids are about 0.5 cm to about 1 cm in length and about 0.4 cm to about 0.8 cm in width at the widest point. Petaloids are shaped somewhat round to oval with rounded apices.

NEWLY OPENED FLOWER

The under surface color of the outer petals is near between 35c and 35d. At the point where the petal attaches, there is a moderately large zone of near between 19a and 19b. The upper surface color of the outer petals is near between 35b and 35c. At the point where the petal attaches, there is a very large zone of near between 19a and 19b.

The under and upper surface color of the intermediate petals is near between 19a and 35c.

The under surface color of the inner petals is near between 19a and 19d with some edges suffused with near between 36a and 35d. The upper surface color of the inner petals is near between 19a and 19b.

The under and upper surface color of the petaloids are similar in coloration to the upper and under surfaces of the intermediate and inner petals.

The general tonality of the newly opened flower is near between 19a and 19b, with near between 35b and 35c on the outer apices.

THREE-DAY OLD FLOWER

The under surface color of the outer petals is near between 35d and 36a. At the point where the petal attaches, there is a moderately small zone of near between 19b and 19c. The upper surface color of the outer petals is near between 35c and 35d.

The under and upper surface color of the inner petals is near between 19a and 19d.

The under and upper surface color of the petaloids are similar in coloration to the upper and under surfaces of the intermediate and inner petals.

The general tonality of the three-day-old flower is near between 19a and 19c, with near between 35c and 35d on the outer apices.

On the spent bloom, the petals usually all drop off cleanly except for some petaloids that persist. In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few many in number (average about 120) and are arranged regularly about the pistils; a few are mixed with petaloids or tucked in the calyx. The filaments are of very moderately somewhat short to medium to long length (about 0.5 cm to about 1.4 cm.) few to many to most with without anthers. Filaments are near between 13b and 12b in color. The anthers are medium for the class and all open approximately at the same time. Anther color is near between 23b and 12c when immature and near between 200b and 167b at maturity. Pollen is abundant and near between 17c and 15b in color.

FEMALE REPRODUCTIVE ORGANS

Pistils vary in number (average about 80). The styles are uneven, long in length (about 0.5 cm to about 1.3 cm.), average in caliper, loosely bunched. Stigma color is near between 13c and 12b. Style color is near between 149d and 150d. Ovaries are usually enclosed in the calyx, although some may protrude from the calyx.

Hips have not been observed on this variety when grown in Wasco, Calif.

FOLIAGE

The compound leaves are usually comprised of three to five and are borne in normal quantities. The five-leaflet leaves are about 12.5 cm to about 15.5 cm in length and about 10 cm to about 13 cm in width at the widest point, moderately crisp in texture, and matte in finish. The terminal leaflets are about 5.5 cm to about 8.1 cm in length and about 3.2 to about 5 cm in width at the widest point, shaped ovate with obtuse apices and round bases. Their margins are serrate.

The upper and under surface color of the mature leaf is near between 137a and 137b. The under surface color of the mature leaf is near between 145a and 145b. The upper and under surface color of the young leaf is near between 138a and 138b. The under surface color of the young leaf is near between 145b and 145c.

The rachis average in caliper and rough. The upper side is moderately grooved with few some many hairs and stipitate glands and prickles on the edges of the grooves. The under side of the rachis is rough with few hairs and stipitate glands and small prickles. The rachis color is near between 144c and 144d.

The stipules are about 1.2 cm to about 1.4 cm in length narrow width to wide (about 1 cm to about 1.5 cm) with medium points that usually turn out at an angle of 45 degrees toward the stem. The stipules color is near between 146c and 146b.

The petiole is average in caliper and rough. The upper side is moderately shallowly grooved with some hairs and stipitate glands and prickles on the edges of the grooves. The under side of the rachis is rough with some hairs and stipitate glands and small prickles. The petiole color is near between 146b and 146c.

The plant displays an average above average degree of resistance to powdery mildew and rust as compared to other commercial varieties grown under comparable conditions in Wasco, Calif. The plant's winter hardiness and drought/heat tolerance are yet to be determined.

GROWTH

The plant has a upright medium growth habit (about 150 to about 180 cm in height and about 40 to about 60 cm spread at the widest point), with full branching. It displays vigorous growth and the canes are medium to caliper for the class.

The color of the major stems is near between 148a and 148b. They bear large prickles that are about 0.07 cm to about 1.1 cm. in length. The large hooked prickles angle slightly downward to rounded base; prickle color is near 166c. The major stem has few prickles of similar shape and coloration and which are near between 166c and 166d in color.

The color of the branches is near between 148a and 146c. They bear few large prickles which are of similar size and shape to the large prickles on the major stems; prickle color is near between 166c and 166d. The branches bear few small prickles of similar shape and coloration and which are near between 166c and 166d in color. There are no coarse hairs.

The color of the new shoots is near between 144a and 148b. They bear few large prickles which are of similar size and shape to the large prickles on the major stems; prickle color is near between 166c.

I claim:

1. A new and distinct Hybrid Tea rose plant of the variety substantially as described and illustrated herein.

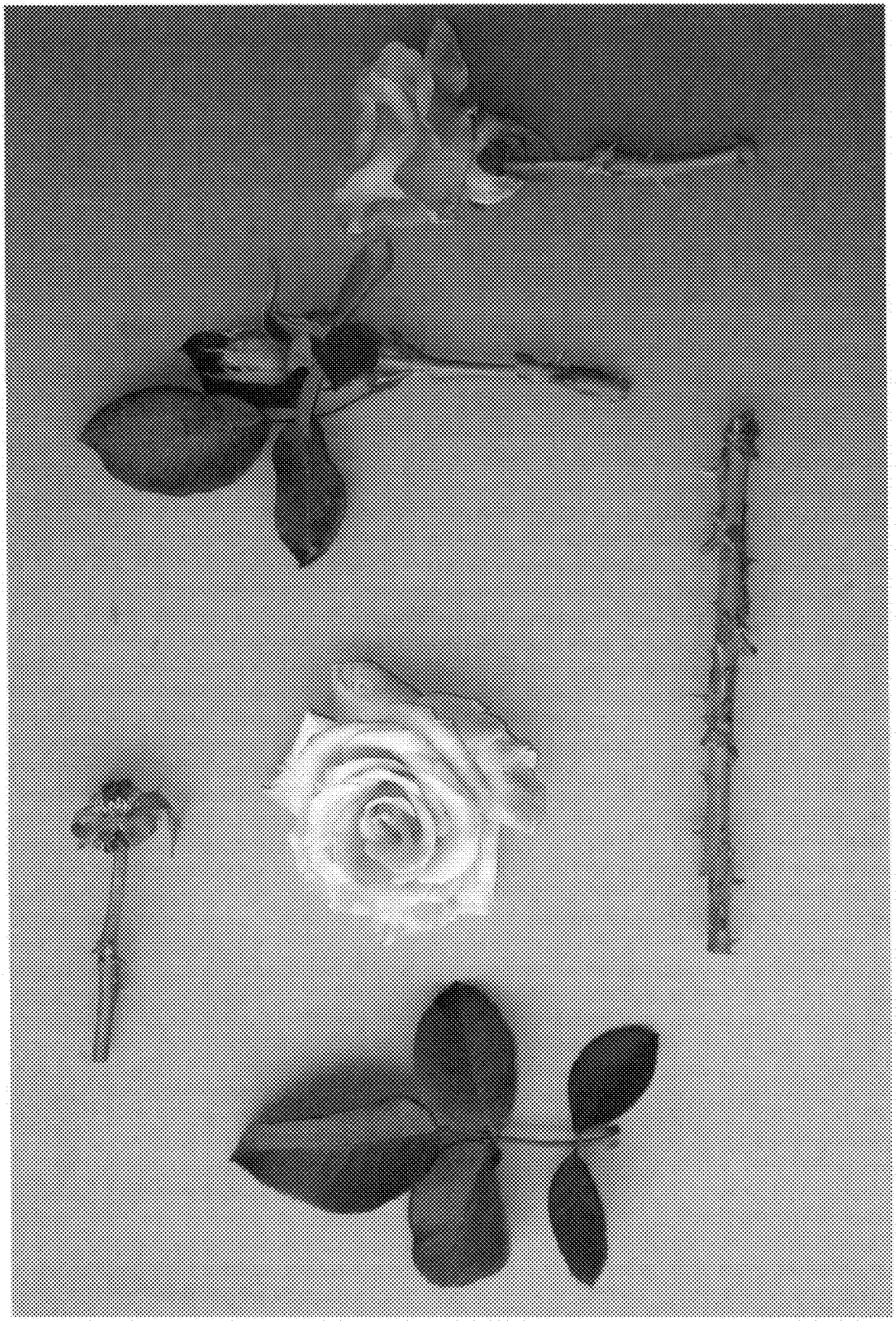

* * * * *